United States Patent [19]

Hynes

[11] Patent Number: 4,683,235

[45] Date of Patent: Jul. 28, 1987

[54] ANALGESIC METHOD

[75] Inventor: Martin D. Hynes, Carmel, Ind.

[73] Assignee: Eli Lilly and Company, Indianapolis, Ind.

[21] Appl. No.: 889,157

[22] Filed: Jul. 25, 1986

Related U.S. Application Data

[63] Continuation of Ser. No. 705,176, Feb. 25, 1985, abandoned.

[51] Int. Cl.$^4$ .................... A61K 31/44; A61K 31/135
[52] U.S. Cl. ...................................... 514/282; 514/651
[58] Field of Search ................................ 514/282, 651

[56] References Cited

U.S. PATENT DOCUMENTS

| | | | |
|---|---|---|---|
| 4,035,511 | 7/1977 | Messing et al. | 424/330 |
| 4,083,982 | 4/1978 | Messing et al. | 424/260 |
| 4,313,896 | 2/1982 | Molloy et al. | 260/501.18 |
| 4,314,081 | 2/1982 | Molloy et al. | 564/347 |

OTHER PUBLICATIONS

Chem. Abst. 92 (1980) 191195z.
Hynes et al., *Drug Development Research*, 2, 33 (1982).
Messing et al., *Psychopharmacology Communications*, 1(5), 511 (1975).
Larson et al., *Life Sciences*, 21, 1807 (1977).
Sugrue et al., *J. Pharm. Pharmac.*, 28, 447 (1976).

*Primary Examiner*—Stanley J. Friedman
*Attorney, Agent, or Firm*—Robert A. Conrad; Leroy Whitaker

[57] ABSTRACT

This invention provides a method of producing analgesia in mammals which comprises administering codeine and fluoxetine or norfluoxetine. Pharmaceutical formulations useful in this method are also provided.

9 Claims, No Drawings

ANALGESIC METHOD

This application is a continuation of application Ser. No. 705,176, filed Feb. 25, 1985, now abandoned.

BACKGROUND OF THE INVENTION

Fluoxetine [3-(4-trifluoromethylphenoxy)-N-methyl-3-phenylpropylamine] has been shown to be a highly specific inhibitor of serotonin uptake. See Fuller et al., *J. Pharm. Exp. Ther.*, 193, 796 (1975) and Wong et al., id., 804 (1975). In addition, fluoxetine has been shown to possess analgesic properties when administered alone (U.S. Pat. No. 4,035,511) or when given with morphine (U.S. Pat. No. 4,083,982). Whether this latter activity is described as a synergistic effect or that of fluoxetine potentiating the morphine analgesic activity appears to depend upon the test system employed to demonstrate the analgesic activity. See Messing et al., *Psychopharmacology Comm.*, 1, 511 (1975); Sugrue et al., *J. Pharm. Pharmac.*, 28, 447 (1976); Larson et al., *Life Sci.*, 21, 1807 (1977); and Hynes et al., *Drug Dev. Res.*, 2, 33 (1982).

Norfluoxetine [3-(4-trifluoromethylphenoxy)-3-phenylpropylamine] is a metabolite of fluoxetine and is also known to block monoamine uptake, especially serotonin. See U.S. Pat. No. 4,313,896.

It is desirable to find methods of causing analgesia which result in few, if any, adverse side effects to the patient. Thus, a method of potentiating the analgesic effect of analgesics, such as codeine, would enable one to employ less codeine to achieve the desired analgesic effect while limiting side effects normally associated with higher doses of the analgesic.

SUMMARY OF THE INVENTION

This invention provides a method of potentiating codeine analgesia in mammals, either alone or in combination with aspirin or acetaminophen, which comprises the administration of an effective amount of fluoxetine or norfluoxetine prior to, concomitantly with, or after the administration of an amount of codeine which, if given alone, would produce less than the desired analgesic effect. This method is useful in that lower doses of codeine are required to produce analgesia thereby resulting in fewer undesired side effects, such as physical dependence, tolerance, and respiratory depression.

This invention also provides a pharmaceutical formulation comprising a combination of codeine and either fluoxetine or norfluoxetine or salts thereof, optionally in further combination with aspirin or acetaminophen. The formulations are useful for practicing the analgesic method described above.

DETAILED DESCRIPTION AND PREFERRED EMBODIMENTS

When used throughout this description, the terms "codeine," "fluoxetine," and "norfluoxetine" are meant to include not only the parent free base compounds, but also the recognized pharmaceutically acceptable acid addition salts of the respective compounds. Especially preferred salts of each compound are mineral acid salts such as the hydrochloride, sulfate, and phosphate salts. An especially preferred combination of compounds consists of codeine sulfate together with fluoxetine hydrochloride.

The combination of fluoxetine or norfluoxetine and low doses of codeine is useful in three ways. First, the combination of fluoxetine or norfluoxetine and a dose of codeine that otherwise would not result in analgesia has been found to provide a useful analgesic effect. Second, the combination of fluoxetine or norfluoxetine and an analgesic dose of codeine can yield greater analgesia than the same dose of codeine alone. Finally, the combination of codeine and fluoxetine or norfluoxetine results in analgesia even when there is tolerance to codeine alone. The ability to employ lesser amounts of codeine than normally required to achieve the same analgesic effect is desirable in order to limit physical dependence, tolerance, and respiratory depression, as well as other adverse side effects normally associated with chronic administration of codeine. In addition, it is apparent that the combination provided by this invention is useful for producing analgesia even in patients who have become tolerant to codeine alone.

The ability of fluoxetine or norfluoxetine to potentiate the analgesic effect of codeine was demonstrated in the mouse writhing assay. Writhing, which is characterized by contraction of the abdominal musculature, extension of the hindlegs, and rotation of the trunk, was induced in albino male mice. The extent to which writhing is reduced following administration of a test compound is an indication of the analgesic activity of that compound.

Mice, weighing 18-24 grams, were fasted overnight and given the test compounds by gavage or subcutaneously. Writhing was then induced by the intraperitoneal administration of acetic acid (0.55 to 0.60 percent). Each treatment group consisted of five mice. The total number of writhes for the treatment group was determined during a 10-minute observation period starting five minutes after acetic acid administration. Control groups had a total of 40-60 writhes per mouse during the observation period. The results in the mouse writhing assay are presented either as the effective dose in mg/kg of the respective test compound required to inhibit induced writhing in the test animals by fifty percent ($ED_{50}$), or as the percent inhibition of writhing at the particular dose of the test compound administered.

In this test system, fluoxetine hydrochloride was found to be devoid of analgesic activity when administered at doses up to 160 mg/kg 30-180 minutes before writhing was induced. However, fluoxetine was found to potentiate an inactive dose of codeine in a manner that was dependent upon the dose of fluoxetine as summarized in Table 1. The oral administration of 10 mg/kg of codeine sulfate to a mouse 60 minutes prior to the assessment of writhing provided no inhibition of the writhing. However, when a 10, 20, or 40 mg/kg dose of fluoxetine hydrochloride was administered together with the codeine sulfate, inhibition of mouse writhing increased in a dose dependent and statistically significant manner. These data demonstrate that the combination of fluoxetine with a low dose of codeine, one that otherwise would not produce analgesia, provides significant analgesia in this test system.

TABLE 1

| Fluoxetine Dose Dependently Potentiates an Inactive Dose of Codeine Sulfate | | |
|---|---|---|
| Codeine Sulfate[1] (mg/kg) | Fluoxetine Hydrochloride[1] (mg/kg) | Percent Inhibition of Mouse Writhing |
| 10 | 0 | 0 |
| 10 | 10 | 22* |
| 10 | 20 | 30* |

TABLE 1-continued

Fluoxetine Dose Dependently Potentiates
an Inactive Dose of Codeine Sulfate

| Codeine Sulfate[1] (mg/kg) | Fluoxetine Hydrochloride[1] (mg/kg) | Percent Inhibition of Mouse Writhing |
|---|---|---|
| 10 | 40 | 73* |

[1]Fluoxetine hydrochloride and codeine sulfate were administered simultaneously by the oral route. Writhing was assessed 60 minutes later.
*Significantly different (p < 0.05) from codeine sulfate alone by the Student's t test.

The $ED_{50}$ of codeine sulfate was determined to be 27.0 mg/kg in a second experiment when administered orally 60 minutes prior to assessment of writhing. As indicated in Table 2, the addition of 20 mg/kg of fluoxetine hydrochloride administered orally together with codeine sulfate provided an $ED_{50}$ of almost one-half the control experiment where codeine sulfate was administered alone.

TABLE 2

Enhancement of Codeine Sulfate Analgesic Activity by Fluoxetine Hydrochloride

| Fluoxetine Hydrochloride[1] | Codeine Sulfate Inhibition of Mouse Writhing $ED_{50}$ (mg/kg) |
|---|---|
| 0 | 27.0 |
| 20 | 15.4 |

[1]Fluoxetine hydrochloride and codeine sulfate were administered simultaneously by the oral route. Writhing was assessed 60 minutes later.

The data presented in Table 3 show that when fluoxetine hydrochloride was administered orally three hours prior to the assessment of codeine sulfate analgesia, the $ED_{50}$ of codeine sulfate administered orally 15 minutes prior to the assessment of writhing was found to be half of that observed when saline was administered in place of the fluoxetine.

TABLE 3

Enhancement of Codeine Sulfate Analgesia in the Mouse Writhing Assay by Pretreatment with Fluoxetine Hydrochloride

| Pretreatment[1] | Codeine Sulfate Inhibition of Mouse Writhing $ED_{50}$ (mg/kg)[2] |
|---|---|
| Saline | 18.6 |
| Fluoxetine Hydrochloride (20 mg/kg) | 9.4 |

[1]Saline or fluoxetine hydrochloride was orally administered three hours prior to the assessment of codeine analgesia.
[2]Codeine sulfate was administered by the oral route 15 minutes prior to the assessment of writhing.

The concomitant administration of codeine and fluoxetine was also shown to increase codeine's analgesic effect over time. As summarized in Table 4, when the two compounds were orally administered simultaneously up to four hours before the assessment of writhing, the combination of 20 mg/kg of fluoxetine hydrochloride and 10 mg/kg of codeine sulfate provided a consistently greater analgesic effect compared to a control experiment where saline was administered in place of fluoxetine.

TABLE 4

Fluoxetine Increases Codeine's Analgesic Action Over Time in the Mouse Writhing Assay

| | Percent Inhibition of Writhing | |
|---|---|---|
| Minutes After Administration[1] | Codeine Sulfate 10 mg/kg + Saline | Codeine Sulfate 10 mg/kg + Fluoxetine Hydrochloride 20 mg/kg |
| 30 | 40 | 71* |
| 60 | 38 | 74* |
| 120 | 37 | 69* |
| 180 | 35 | 45 |
| 240 | 22 | 30 |

[1]Codeine sulfate and fluoxetine hydrochloride were administered simultaneously by the oral route.
*Significantly different (p < 0.05) from codeine sulfate plus saline treatment.

Finally, a comparison of the $ED_{50}$ of codeine sulfate when administered subcutaneously 30 minutes prior to the assessment of mouse writhing was found to be 3.5 times greater than the amount needed when 20 mg/kg of fluoxetine hydrochloride was concomitantly administered by the subcutaneous route as summarized in Table 5.

TABLE 5

Enhancement of Codeine Analgesia by Fluoxetine in the Mouse Writhing Assay

| Fluoxetine Hydrochloride[1] (mg/kg; s.c.) | Codeine Sulfate Induced Inhibition of Mouse Writhing $ED_{50}$ (mg/kg) |
|---|---|
| 0 | 9.8 |
| 20 | 2.8 |

[1]Codeine sulfate and fluoxetine hydrochloride were administered simultaneously by the subcutaneous route. Mouse writhing was assessed 30 minutes later.

The experiments summarized in Tables 2–5 clearly show that a combination of fluoxetine and an analgesic dose of codeine provide greater analgesia than codeine alone. Similarly, it is evident that in order to achieve the same analgesic effect, less codeine is required when fluoxetine is also administered.

The present invention provides a method of causing analgesia in mammals employing codeine in combination with either fluoxetine or norfluoxetine, optionally in combination with aspirin or acetaminophen. The method comprises administering the compounds by any number of routes including the oral, rectal, transdermal, subcutaneous, intravenous, intramuscular, or intranasal routes. The compounds are usually employed in the form of a pharmaceutical composition. The compounds may be administered individually at the same time or different times or together, and by the same route or by different routes. In a preferred embodiment, the compounds are administered orally and together. The potentiating effect of fluoxetine or norfluoxetine is observed when administered up to 24 hours prior to or 2 hours after the administration of codeine. A preferred regimen is the co-administration of both compounds. This co-administration can advantageously be accomplished by the administration of a pharmaceutical formulation comprising both compounds. Accordingly, this invention also provides a pharmaceutical composition comprising from about 1% to about 95% by weight of a mixture of codeine and either fluoxetine or norfluoxetine, optionally in further combination with aspirin or acetaminophen, associated with a pharmaceutically acceptable carrier, excipient, or diluent.

The ratio of the components by weight is preferably from about 4:1 to 1:1 fluoxetine/codeine. An especially preferred ratio is approximately 2:1 fluoxetine/codeine. The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier. The preferred unit dosage forms of the present invention contain from about 10 to about 80 mg of fluoxetine or norfluoxetine and from about 10 to about 60 mg of codeine. In addition, the unit dosage form may contain up to 1000 mg of aspirin or acetaminophen, preferably 200-500 mg of aspirin or 325-650 mg of acetaminophen. However, it will be understood that the specific amount of compounds actually administered will be determined by a physician, in the light of the relevant circumstances including the chosen route of administration, the age, weight, and response of the individual patient, and the severity of the patient's symptoms, and therefore the above dosage ranges are not intended to limit the scope of the invention in any way.

In making the compositions of the present invention, the compounds will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. The compositions thus can be in the form of tablets, pills, powders, lozenges, sachets, cachets, elixirs, suspensions, emulsions, solutions, syrups, aerosols (as a solid or in a liquid medium), ointments containing for example up to 10% by weight of the active compounds, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of all or any of the compounds after administration to the patient by employing procedures well known in the art.

The following examples are provided to further illustrate the formulations by this invention. The examples are illustrative only and are not intended to limit the scope of the invention in any way.

EXAMPLE 1

Hard gelatin capsules are prepared using the following ingredients:

|  | Quantity (mg/capsule) |
| --- | --- |
| Fluoxetine hydrochloride | 60 |
| Codeine sulfate | 40 |
| Starch dried | 350 |
| Magnesium stearate | 10 |

The above ingredients are mixed and filled into hard gelatin capsules in 460 mg quantities.

EXAMPLE 2

A tablet formula is prepared using the ingredients below:

|  | Quantity (mg/tablet) |
| --- | --- |
| Norfluoxetine sulfate | 80 |
| Codeine hydrochloride | 60 |
| Aspirin | 325 |
| cellulose, microcrystalline | 510 |
| Silicon dioxide, fumed | 20 |
| Stearic acid | 5 |

The components are blended and compressed to form tablets each weighing 1000 mg.

EXAMPLE 3

An aerosol solution is prepared containing the following components:

|  | Weight % |
| --- | --- |
| Fluoxetine | 0.18 |
| Codeine phosphate | 0.07 |
| Ethanol | 29.75 |
| Propellant 22 (Chlorodifluoromethane) | 70.00 |

The compounds are mixed with ethanol and the mixture added to a portion of the propellant 22, cooled to −30° and transferred to a filling device. The required amount is then fed to a stainless steel container and diluted with the remainder of the propellant. The valve units are then fitted to the container.

EXAMPLE 4

Tablets are made up as follows:

| Fluoxetine hydrochloride | 70 mg |
| --- | --- |
| Codeine hydrochloride | 30 mg |
| Acetaminophen | 510 mg |
| Starch | 145 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 800 mg |

The active ingredients, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 800 mg.

EXAMPLE 5

Capsules are made as follows:

| | |
|---|---|
| Fluoxetine sulfate | 20 mg |
| Codeine sulfate | 10 mg |
| Aspirin | 65 mg |
| Starch | 59 mg |
| Microcrystalline cellulose | 59 mg |
| Magnesium stearate | 2 mg |
| Total | 215 mg |

The active ingredients, cellulose, starch and magnesium stearate are blended, passed through a No. 45 mesh U.S. sieve, and filled into hard gelatin capsules in 215 mg quantities.

EXAMPLE 6

Suppositories are made as follows:

| | |
|---|---|
| Fluoxetine phosphate | 80 mg |
| Codeine hydrochloride | 60 mg |
| Saturated fatty acid glycerides to | 2,000 mg |

The active ingredients are passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions are made as follows:

| | |
|---|---|
| Norfluoxetine hydrochloride | 70 mg |
| Codeine sulfate | 40 mg |
| Acetaminophen | 325 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicaments are passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

I claim:

1. A method of potentiating codeine analgesia in mammals which comprises the administration to said mammal of an effective potentiating amount of fluoxetine or norfluoxetine in the time range between 24 hours before and 2 hours after the administration of codeine.

2. The method of claim 1 wherein the compounds are administered simultaneously.

3. The method of claim 2 employing fluoxetine hydrochloride.

4. The method of claim 3 wherein about 10 to about 80 mg of fluoxetine hydrochloride and from about 10 to about 60 mg of codeine sulfate are administered.

5. A pharmaceutical formulation which comprises fluoxetine or norfluoxetine, codeine, and a pharmaceutically acceptable carrier, diluent, or excipient therefor wherein the ratio of fluoxetine or norfluoxetine to codeine is about 7:1 to about 1:1 and the combination of active ingredients is present in an effective amount.

6. A formulation according to claim 5 employing fluoxetine hydrochloride.

7. A formulation according to claim 6 wherein the ratio of fluoxetine hydrochloride to codeine sulfate is approximately 2:1.

8. A formulation according to claim 7 employing from about 10 to about 80 mg of fluoxetine hydrochloride and from about 10 to about 60 mg of codeine sulfate.

9. A formulation according to claim 8 which is formulated for oral administration.

* * * * *